(12) United States Patent
Nobe et al.

(10) Patent No.: US 8,097,745 B2
(45) Date of Patent: Jan. 17, 2012

(54) METHOD OF PRODUCING ORGANOSILICON COMPOUND

(75) Inventors: Yohei Nobe, Tsuchiura (JP); Kang-go Chung, Tsukuba (JP); Ryuichi Saito, Tokyo (JP)

(73) Assignee: JSR Corporation, Tokyo (JP)

( * ) Notice: Subject to any disclaimer, the term of this patent is extended or adjusted under 35 U.S.C. 154(b) by 91 days.

(21) Appl. No.: 12/749,735

(22) Filed: Mar. 30, 2010

(65) Prior Publication Data

US 2011/0082309 A1 Apr. 7, 2011

(30) Foreign Application Priority Data

Mar. 30, 2009 (JP) ................................. 2009-81032

(51) Int. Cl.
*C07F 7/18* (2006.01)

(52) U.S. Cl. ........ 556/467; 556/466; 556/470; 556/478; 556/481

(58) Field of Classification Search .................. 556/467, 556/466, 470, 478, 481
See application file for complete search history.

(56) References Cited

U.S. PATENT DOCUMENTS

| | | | |
|---|---|---|---|
| 5,430,168 A | 7/1995 | Ferguson et al. | |
| 7,160,625 B2 | 1/2007 | Hara et al. | |
| 7,291,567 B2 | 11/2007 | Tsuchiya et al. | |
| 7,399,715 B2 | 7/2008 | Tsuchiya et al. | |
| 7,413,775 B2 | 8/2008 | Hara et al. | |
| 7,462,678 B2 | 12/2008 | Akiyama et al. | |
| 7,514,151 B2 | 4/2009 | Shiota | |
| 7,528,207 B2 | 5/2009 | Nakagawa et al. | |
| 2006/0151884 A1 | 7/2006 | Hara et al. | |
| 2006/0210812 A1 | 9/2006 | Shiota | |
| 2007/0015892 A1 | 1/2007 | Nakagawa et al. | |
| 2007/0020467 A1 | 1/2007 | Nakagawa et al. | |
| 2007/0027287 A1 | 2/2007 | Akiyama et al. | |
| 2007/0031687 A1 | 2/2007 | Akiyama et al. | |
| 2008/0038527 A1 | 2/2008 | Akiyama et al. | |
| 2008/0246153 A1 | 10/2008 | Tsuchiya et al. | |
| 2008/0268264 A1 | 10/2008 | Akiyama et al. | |
| 2009/0281237 A1 | 11/2009 | Nakagawa et al. | |
| 2009/0299086 A1 | 12/2009 | Nobe et al. | |
| 2010/0007025 A1* | 1/2010 | Nakagawa et al. | |

FOREIGN PATENT DOCUMENTS

| | | |
|---|---|---|
| JP | 07-206874 | 8/1995 |
| JP | 08-208666 | 8/1996 |
| JP | 2002-167438 | 6/2002 |
| JP | 2005-047852 | 2/2005 |
| JP | 2005-051192 | 2/2005 |
| JP | 01-313528 | 7/2005 |

OTHER PUBLICATIONS

U.S. Appl. No. 12/934,806, filed Sep. 27, 2010, Nakagawa et al.
U.S. Appl. No. 12/527,327, filed Aug. 14, 2009, Nakagawa, et al.
U.S. Appl. No. 12/717,225, filed Mar. 4, 2010, Akiyama, et al.

* cited by examiner

*Primary Examiner* — Elvis O Price
(74) *Attorney, Agent, or Firm* — Oblon, Spivak, McClelland, Maier & Neustadt, L.L.P.

(57) ABSTRACT

A simple method of producing an organosilicon compound of a formula $R^2_n(OR^4)_mSi-R^1-Si(OR^4)_mR^2_n$ is disclosed. The method comprises the following two steps, $$Y-R^1-Y+SiX_{m+1}R^2_n \rightarrow R^2_nX_mSi-R^1-SiX_mR^2_n$$

$$R^2_nX_mSi-R^1-SiX_mR^2_n+M(OR^4)_r \rightarrow R^2_n(OR^4)_mSi-R^1-Si(OR^4)_mR^2_n$$

In the formulas, $R^1$ is methylene, alkylene, or arylene, $R^2$ is alkyl, alkenyl, alkynyl, or aryl, m and n is 0 to 3, provided m+n=3, at least one m being 1 or more, Y is halogen, X is hydrogen or halogen, $R^4$ is alkyl, alkenyl, alkynyl, or aryl, M is metal, and r is the valence of the metal). The organosilicon compound is used to form a film having excellent heat resistance, chemical resistance, conductivity, and modulus of elasticity.

7 Claims, No Drawings

METHOD OF PRODUCING ORGANOSILICON COMPOUND

Japanese Patent Application No. 2009-81032 filed on Mar. 30, 2009 is hereby incorporated by reference in its entirety.

BACKGROUND OF THE INVENTION

The present invention relates to a method of producing an organosilicon compound.

A silicon compound having a hydrolyzable group such as an alkoxy group or a halogen atom is used as an inorganic polymer material precursor or a CVD raw material. A film formed using an organosilicon compound having a skeleton in which two silicon atoms are bonded via at least one carbon atom has excellent chemical and mechanical properties (e.g., heat resistance, chemical resistance, conductivity, and modulus of elasticity) (see WO 2005/068539).

An organosilicon compound having a skeleton in which two silicon atoms are bonded via a carbon atom may be synthesized by hydrosilylation using a transition metal as a catalyst, or forming a silicon-carbon bond by a nucleophilic reaction (Grignard reaction) using an alkali metal, for example. WO 2005/068539 discloses a method of producing an organosilicon compound that includes reacting methyltrimethoxysilane with a Grignard reagent obtained by reacting (chloromethyl)trimethylsilane with magnesium to obtain [(trimethylsilyl)methyl]methyldimethoxysilane.

However, when producing the above organosilicon compound using the method disclosed in WO 2005/068539, it is necessary to control the conditions for suppressing polymerization due to a side reaction since the hydrolyzable group has high reactivity. Particularly, when synthesizing an organosilicon compound having a skeleton with two silicon atoms bonded via a carbon atom in which the two silicon atoms both have an alkoxy group, suppression of polymerization due to a side reaction is particularly important. It is not necessarily easy to arbitrarily control the number of alkoxy groups on each end. Therefore, development of a versatile method that can easily synthesize an organosilicon compound having a skeleton with two silicon atoms bonded via a carbon atom in which the two silicon atoms both have an alkoxy group has been desired.

SUMMARY OF THE INVENTION

An object of the invention is to provide a method of producing an organosilicon compound by which a product can be obtained in high yield by a simple process.

According to one aspect of the invention, there is provided a method of producing an organosilicon compound comprising: reacting a compound shown by the following formula (4) and a compound shown by the following formula (5) to produce a compound shown by the following formula (1); and reacting the compound shown by the following formula (1) and a metal compound shown by the following formula (2) to produce an organosilicon compound shown by the following formula (3), $$R^2{}_n X_m Si-R^1-SiX_m R^2{}_n \qquad (1)$$

wherein $R^1$ represents a methylene group, an alkylene group having 2 to 10 carbon atoms, or an arylene group having 6 to 12 carbon atoms, $R^2$ individually represents an alkyl group having 1 to 10 carbon atoms, an alkenyl group having 2 to 10 carbon atoms, an alkynyl group having 2 to 10 carbon atoms, or an aryl group having 6 to 12 carbon atoms, X individually represents a hydrogen atom or a halogen atom, and m and n individually represent an integer from 0 to 3, provided that m+n=3, at least one m being 1 or more, $$M(OR^4)_r \qquad (2)$$

wherein M represents a metal element, r represents the valence of the metal element, and $R^4$ individually represents an alkyl group having 1 to 10 carbon atoms, an alkenyl group having 2 to 10 carbon atoms, an alkynyl group having 2 to 10 carbon atoms, or an aryl group having 6 to 12 carbon atoms, $$R^2{}_n(OR^4)_m Si-R^1-Si(OR^4)_m R^2{}_n \qquad (3)$$

wherein $R^1$, $R^2$, m, and n are the same as defined for the formula (1), and $R^4$ is the same as defined for the formula (2), $$Y-R^1-Y \qquad (4)$$

wherein Y represents a halogen atom, and $R^1$ is the same as defined for the formula (1), $$SiX_{m+1}R^2{}_n \qquad (5)$$

wherein X, $R^2$, m, and n are the same as defined for the formula (1).

In the above method of producing an organosilicon compound, $R^1$ in the formula (1) and the formula (2) may be a methylene group.

In the above method of producing an organosilicon compound, M in the formula (2) may be at least one metal element selected from an alkali metal element and an alkaline earth metal element. In this case, M in the formula (2) may be sodium.

In the above method of producing an organosilicon compound, $R^2$ in the formula (1) may individually represents an alkyl group having 1 to 10 carbon atoms, an alkenyl group having 2 to 10 carbon atoms, or an aryl group having 6 to 12 carbon atoms.

In the above method of producing an organosilicon compound, $R^2$ in the formula (1) may individually represents an alkyl group having 1 to 10 carbon atoms or an alkenyl group having 2 to 10 carbon atoms.

In the above method of producing an organosilicon compound, $R^2$ in the formula (1) may individually represents an alkyl group having 1 to 10 carbon atoms.

According to the above method of producing an organosilicon compound, the group shown by X in the organosilicon compound shown by the formula (1) can be converted into a group $OR^4$ by reacting the organosilicon compound shown by the formula (1) with the metal compound shown by the formula (2). This makes it possible to obtain a product (organosilicon compound shown by the formula (3)) in high yield by a simple process.

DETAILED DESCRIPTION OF THE EMBODIMENT

An organosilicon compound and a method of producing the same according to one embodiment of the invention are described in detail below.

1. Method of Producing Organosilicon Compound 1.1. Method of Producing Organosilicon Compound A method of producing an organosilicon compound according to one embodiment of the invention includes reacting an organosilicon compound shown by the following formula (1) (hereinafter may be referred to as "compound 1") and a metal compound shown by the following formula (2) (hereinafter may be referred to as "compound 2") to produce an organosilicon compound shown by the following formula (3) (hereinafter may be referred to as "compound 3"), $$R^2_n X_m Si-R^1-SiX_m R^2_n \quad (1)$$

wherein $R^1$ represents a substituted or unsubstituted methylene group, a substituted or unsubstituted alkylene group having 2 to 10 carbon atoms, or a substituted or unsubstituted arylene group having 6 to 12 carbon atoms, $R^2$ individually represents a substituted or unsubstituted alkyl group having 1 to 10 carbon atoms, a substituted or unsubstituted alkenyl group having 2 to 10 carbon atoms, a substituted or unsubstituted alkynyl group having 2 to 10 carbon atoms, or a substituted or unsubstituted aryl group having 6 to 12 carbon atoms, X individually represents a hydrogen atom or a halogen atom, and m and n individually represent an integer from 0 to 3, provided that m+n=3, at least one m being 1 or more, $$M(OR^4)_r \quad (2)$$

wherein M represents a metal element, r represents the valence of the metal element, and $R^4$ individually represents a substituted or unsubstituted alkyl group having 1 to 10 carbon atoms, a substituted or unsubstituted alkenyl group having 2 to 10 carbon atoms, a substituted or unsubstituted alkynyl group having 2 to 10 carbon atoms, or a substituted or unsubstituted aryl group having 6 to 12 carbon atoms, $$R^2_n(OR^4)_m Si-R^1-Si(OR^4)_m R^2_n \quad (3)$$

wherein $R^1$, $R^2$, m, and n are the same as defined for the formula (1), and $R^4$ is the same as defined for the formula (2).

As examples of a substituted or unsubstituted alkylene group having 2 to 10 carbon atoms represented by $R^1$ in the formulas (1) and (3), a dimethylene group, a trimethylene group, a tetramethylene group, a pentamethylene group, a hexamethylene group, a heptamethylene group, an octamethylene group, a nonamethylene group, and a decamethylene group can be given, and as examples of a substituted or unsubstituted arylene group having 6 to 12 carbon atoms represented by $R^1$, a phenylene group and a naphthylene group can be given. The methylene group, the alkylene group, and the arylene group may be either substituted or unsubstituted. A halogen atom can be given as an example of a substituent.

In the formulas (1) and (3), examples of a substituted or unsubstituted alkyl group having 1 to 10 carbon atoms represented by $R^2$ include a methyl group, an ethyl group, an n-propyl group, an isopropyl group, an n-butyl group, an isobutyl group, a tert-butyl group, a pentyl group, an isopentyl group, a hexyl group, a heptyl group, an octyl group, a nonyl group, and a decyl group. Examples of a substituted or unsubstituted alkenyl group having 2 to 10 carbon atoms represented by $R^2$ include a vinyl group, an allyl group, a butenyl group, and a hexenyl group. Examples of a substituted or unsubstituted alkynyl group having 2 to 10 carbon atoms represented by $R^2$ include an ethynyl group and a propynyl group. Examples of a substituted or unsubstituted aryl group having 6 to 12 carbon atoms represented by $R^2$ include a phenyl group, a tolyl group, and a naphthyl group. The alkyl group, the alkenyl group, the alkynyl group, and the aryl group may be either substituted or unsubstituted, and a halogen atom can be given as a substituent.

In the formulas (2) and (3), examples of a substituted or unsubstituted alkyl group having 1 to 10 carbon atoms represented by $R^4$ include a methyl group, an ethyl group, an n-propyl group, an isopropyl group, an n-butyl group, an isobutyl group, a tert-butyl group, a pentyl group, an isopentyl group, a hexyl group, a heptyl group, an octyl group, a nonyl group, and a decyl group. Examples of a substituted or unsubstituted alkenyl group having 2 to 10 carbon atoms represented by $R^4$ include a vinyl group, an allyl group, a butenyl group, and a hexenyl group. Examples of a substituted or unsubstituted alkynyl group having 2 to 10 carbon atoms represented by $R^4$ include an ethynyl group and a propynyl group. Examples of a substituted or unsubstituted aryl group having 6 to 12 carbon atoms represented by $R^4$ include a phenyl group, a tolyl group, and a naphthyl group. The alkyl group, the alkenyl group, the alkynyl group, and the aryl group may be either substituted or unsubstituted, and a halogen atom can be given as a substituent.

As examples of M in the formula (2), an alkali metal element, an alkaline earth metal element, and the like can be given. As an alkaline metal element (monovalent), sodium, potassium, and the like can be given, and as an alkaline earth metal element (divalent), calcium, magnesium, and the like can be given. M is preferably an alkali metal element, and more preferably sodium.

In the formulas (1) and (3), $R^1$ is preferably a methylene group or a phenylene group, and more preferably a methylene group. An alkyl group represented by $R^2$ is preferably an n-propyl group, an isopropyl group, an n-butyl group, an isobutyl group, a tert-butyl group, a pentyl group, an isopentyl group, a hexyl group, a heptyl group, an octyl group, or a nonyl group, and an alkenyl group represented by $R^2$ is preferably an allyl group, a butenyl group, or a hexenyl group. More preferably, $R^2$ represents a methyl group, an ethyl group, an n-propyl group, a vinyl group, and a phenyl group, with a methyl group being particularly preferable. X preferably represents a hydrogen atom, a chlorine atom, or a bromine atom.

$R^4$ in the formulas (2) and (3) is preferably a methyl group, an ethyl group, an n-propyl group, or an isopropyl group, and more preferably a methyl group, an ethyl group, or an isopropyl group, with a methyl group being still more preferable.

In the formula (1) and (3), two m are preferably the same and two n are preferably the same. m is preferably 1 or 2, and more preferably 2. n is preferably 1 or 2, and more preferably 1.

As examples of the compound 1 (raw material), bis(dichloromethylsilyl)methane, bis(dichloromethylsilyl)ethane, trimethylsilylmethyldichlorosilane, trimethylsilylethyldichlorosilane, bis(chloromethylsilyl)methane, bis(chloromethylsilyl)ethane, bis(chlorodimethylsilyl)methane, bis(chlorodimethylsilyl)ethane, and p-(dichlorosilyl)benzene can be given.

As examples of the compound 2, a metal alkoxide such as sodium methoxide and sodium ethoxide can be given.

As examples of the compound 3 (target compound), bis(dimethoxymethylsilyl)methane, bis(diethoxymethylsilyl)methane, bis(dimethoxymethylsilyl)ethane, bis(diethoxymethylsilyl)ethane, trimethylsilylmethyltrimethoxysilane, trimethylsilylmethyltriethoxysilane, trimethylsilylethyltrimethoxysilane, trimethylsilylethyltriethoxysilane, bis(methoxydimethylsilyl)methane, bis(methoxydimethylsilyl)ethane, bis(ethoxydimethylsilyl)methane, bis(ethoxydimethylsilyl)ethane, bis(trimethoxysilyl)benzene, and bis(triethoxysilyl)benzene can be given.

1.2. Production of Compound 3

In the production of the compound 3, a compound 2 is used usually at a molar ratio of 1 to 10 with respect to a compound 1. The reaction for producing the compound 3 is carried out at a temperature of usually 0 to 100° C. for a period of usually for 1 to 10 hours.

In the method of producing an organosilicon compound according to this embodiment, a solvent used when reacting the compound 1 with the compound 2 is preferably an alcohol shown by the formula $R^4OH$ (wherein $R^4$ is the same as the $R^4$ in the formula (2)) in order to prevent substitution of a functional group in the product (compound 3).

1.3 Production of Compound (1) (Raw Material)

The method of producing an organosilicon compound according to this embodiment may further include reacting at least one compound shown by the following formula (4) (hereinafter may be referred to as "compound 4") with a compound shown by the following formula (5) (hereinafter may be referred to as "compound 5") to produce the compound shown by the formula (1).

$$Y-R^1-Y \qquad (4)$$

wherein Y represents a halogen atom, and $R^1$ is the same as defined for the formula (1), $$SiX_{m+1}R^2_n \qquad (5)$$

wherein X, $R^2$, m, and n are the same as defined for the formula (1).

In the reaction of the compound 4 with the compound 5 to obtain the compound 1, the compound 1 having a skeleton of $Si-R^1-Si$ is obtained by a Grignard reaction between the compound 4 and the compound 5.

When reacting the compound 4 with the compound 5, the compound 5 is used in an amount of 0.7 to 10 mol, and more preferably 2 to 5 mol, per 1 mol of the compound 4. The reaction temperature is preferably −15° C. to 150° C., and more preferably 0 to 40° C.

As examples of the compound 4, dibromomethane, dichloromethane, dibromoethane, dichloroethane, dichlorobenzene, and dibromobenzene can be given.

As examples of the compound 5, chlorodimethylsilane, bromodimethylsilane, dichloromethylsilane, dibromomethylsilane, dichloroethylsilane, dibromoethylsilane, trichloromethylsilane, and trichloroethylsilane can be given.

It is preferable to use an ether solvent when producing the compound 1. Examples of the ether solvent include diethyl ether, di-n-propyl ether, diisopropyl ether, dibutyl ether, ethyl propyl ether, anisole, phenetole, diphenyl ether, diethylene glycol dimethyl ether, diethylene glycol diethyl ether, diethylene glycol dibutyl ether, diethylene glycol methyl ethyl ether, dipropylene glycol dimethyl ether, dipropylene glycol diethyl ether, dipropylene glycol dibutyl ether, dipropylene glycol methyl ethyl ether, ethylene glycol dimethyl ether, ethylene glycol diethyl ether, ethylene glycol dibutyl ether, ethylene glycol methyl ethyl ether, propylene glycol dimethyl ether, propylene glycol diethyl ether, propylene glycol dibutyl ether, propylene glycol methyl ethyl ether, tetrahydrofuran, and dioxane. Among these, diethyl ether, tetrahydrofuran, ethylene glycol dimethyl ether, and ethylene glycol diethyl ether are preferable from the viewpoint of excellent solubility of the compound 4 and the compound 5.

1.4. End Product (Compound 3)

In the method of producing the organosilicon compound according to this embodiment, the compound 3 that is the end product may be used to form an insulating film that includes silicon, carbon, oxygen, and hydrogen, for example. Such an insulating film exhibits high process resistance, that is, the insulating film exhibits resistance to a hydrofluoric acid-based chemical which is widely used for a washing step during a semiconductor production process.

When using the compound 3 as an insulating film-forming material, it is preferable that the compound 3 have a content of elements other than silicon, carbon, oxygen, and hydrogen (hereinafter may be referred to as "impurities") of 10 ppb or less, and a water content of 500 ppm or less, and more preferably 200 ppm or less. An insulating film that exhibits a low relative dielectric constant and excellent process resistance can be obtained in high yield by forming the insulating film using such a compound 3.

It is more preferable to use the compound 3 in which $R^4$ in the formula (3) is a methyl group. Since the compound 3 in which $R^4$ in the formula (3) is a methyl group has a low boiling point, the compound 3 can be conveniently used as a CVD material.

It is more preferable to use the compound 3 in which $R^1$ in the formula (3) is a methylene group. When using the compound 3 in which $R^1$ in the formula (3) is a methylene group, an insulating film exhibiting excellent mechanical strength can be obtained.

1.5. Effects

The method of producing an organosilicon compound according to this embodiment can efficiently produce the compound 3 by converting all groups shown by X in the compound 1 into a group $OR^4$ at one time in the reaction between the compound 1 and the compound 2. This brings about a special effect of efficiently synthesizing the compound 3 in high yield in a simple manner. For example, in the case in which the compound 1 has two or more different groups represented by X, e.g. a hydrogen atom and a halogen atom, the hydrogen atom and the halogen atom can be simultaneously converted into an $OR^4$ group. For this reason, the compound 3 can be obtained in high yield in a simple manner. In the case in which the group represented by X in the compound 1 is a hydrogen atom or a halogen atom, the group shown by X can also be efficiently converted into $OR^4$ group.

When synthesizing the compound 3 without using the method of producing the organosilicon compound according to this embodiment, the compound 3 may be directly obtained by a Grignard reaction, for example between a compound shown by the following formula (6) (hereinafter may be referred to as "compound 6") and a compound shown by the following formula (7) (hereinafter may be referred to as "compound 7"), $$R^2_n(OR^4)_mSi-R^1-M^1X \qquad (6)$$

wherein $R^1$, $R^2$, X, m, and n are the same as defined for the formula (1), $R^4$ is the same as defined for the formula (2), and $M^1$ represents an alkali metal element or an alkaline earth metal element, $$Si(OR^4)_mR^2_n \qquad (7)$$

wherein $R^2$, m, and n are the same as defined for the formula (1) and $R^4$ is the same as defined for the formula (2).

However, when the compound 6 has a hydrolyzable group such as an alkoxy group, the compound 6 polymerizes by self-condensation during the Grignard reaction. As a result, the yield of the compound 3 (i.e., reaction product) may decrease.

On the other hand, the method of producing an organosilicon compound according to this embodiment can produce the compound 3 in high yield by the reaction between the compound 1 and the compound 2.

2. Examples and Comparative Examples

The invention is further described below by way of examples. Note that the invention is not limited to the following examples. In the examples and comparative examples, "%" refers to "wt %" unless otherwise indicated.

2.1. Evaluation Method

The purity of the purified organosilane compound was determined using a gas chromatograph ("6890N" manufactured by Agilent Technologies, column: "SPB-35" manufactured by Supelco). The water content and the impurity content of the purified organosilane compound were measured using a Karl Fisher aquacounter ("AQ-7" manufactured by Hiranuma Sangyo Co., Ltd.) and an atomic absorption spectrophotometer (polarized Zeeman atomic absorption spectrophotometer "Z-5700" manufactured by Hitachi High-Technologies Corporation).

2.2. Synthesis Examples

2.2.1. Synthesis Example 1

A three-necked flask equipped with a cooling condenser and a dropping funnel was dried at 60° C. under reduced pressure, and filled with nitrogen.

Then, the flask was charged with 800 g of tetrahydrofuran, 50 g of magnesium, and 400 g of dichloromethylsilane (compound 5). The contents were stirred for 15 minutes at 40° C. at 300 rpm using a 3:1 motor, with the flask being placed in a water bath. Next, 6 g of dibromomethane (compound 4) was added to the flask. After the internal temperature was increased to 45° C., the water bath was cooled to 25° C. Next, 144 g of dibromomethane was added dropwise using a dropping funnel over 2 hours. After the addition, the mixture was stirred for 6 hours.

The magnesium salt produced as a by-product was filtered and the salt was washed with 200 ml of hexane. The filtrate was concentrated using an evaporator under reduced pressure to obtain 103 g (yield: 72%) of bis(dichloromethylsilyl)methane (compound 1).

The residual water content of the end product was 79 ppm. The content (metal impurity content) of elements other than silicon, carbon, oxygen, and hydrogen was as follows. Specifically, the Na content was 4 ppb, the K content was 6 ppb, the Fe content was 6 ppb, and the Ni content was 2 ppb. The content of each of Li, Fe, Cr, Ag, Cu, Zn, Mn, Co, Ti, Zr, Al, Pb, Sn, and W was equal to or less than the detection limit (0.2 ppb).

2.2.2. Synthesis Example 2

A three-necked flask equipped with a cooling condenser and a dropping funnel was dried at 60° C. under reduced pressure, and filled with nitrogen.

The flask was charged with 59 g of sodium methoxide (compound 2) and 153 g of methanol. The mixture was stirred for 15 minutes at 300 rpm using a 3:1 motor. 86 g of bis(dichloromethylsilyl)methane (compound 1) obtained in the Synthesis Example 1 was then added dropwise over 2 hours using a dropping funnel, with the flask being kept in a water bath at 25° C. After the addition, the mixture was stirred for 2 hours.

The sodium salt produced as a by-product was filtered using a glass filter covered with celite, and the salt was washed with 200 ml of hexane. The filtrate was concentrated using an evaporator under reduced pressure to obtain 100 g (yield: 90%) of bis(dimethoxymethylsilyl)methane (compound 3).

The residual water content of the end product was 114 ppm. The content (metal impurity content) of elements other than silicon, carbon, oxygen, and hydrogen was as follows. Specifically, the Na content was 9 ppb, the K content was 6 ppb, the Fe content was 3 ppb, and the Ni content was 3 ppb. The content of each of Li, Fe, Cr, Ag, Cu, Zn, Mn, Co, Ti, Zr, Al, Pb, Sn, and W was equal to or less than the detection limit (0.2 ppb).

2.2.3. Synthesis Example 3

A three-necked flask equipped with a cooling condenser and a dropping funnel was dried at 60° C. under reduced pressure, and filled with nitrogen.

The flask was charged with 75 g of sodium ethoxide (compound 2) and 220 g of ethanol, and the mixture was stirred for 15 minutes at 300 rpm using a 3:1 motor. 94 g of trimethylsilylmethyldichlorosilane (compound 1) was then added dropwise over 2 hours using a dropping funnel in a water bath at 25° C. After the addition, the mixture was stirred for 2 hours.

The sodium salt produced as a by-product was filtered using a glass filter covered with celite, and the salt was washed with 200 ml of hexane. The filtrate was concentrated under reduced pressure using an evaporator to obtain 89 g (yield: 85%) of trimethylsilylmethyltrimethoxysilane (compound 3).

The residual water content of the end product was 109 ppm. The content (metal impurity content) of elements other than silicon, carbon, oxygen, and hydrogen was as follows. Specifically, the Na content was 8 ppb, the K content was 7 ppb, the Fe content was 8 ppb, and the Ni content was 9 ppb. The content of each of Li, Fe, Cr, Ag, Cu, Zn, Mn, Co, Ti, Zr, Al, Pb, Sn, and W was equal to or less than the detection limit (0.2 ppb).

2.2.4. Synthesis Example 4

A three-necked flask equipped with a cooling condenser and a dropping funnel was dried at 60° C. under reduced pressure, and filled with nitrogen.

The flask was charged with 59 g of sodium methoxide (compound 2) and 153 g of methanol, and the mixture was stirred for 15 minutes at 300 rpm using a 3:1 motor. 94 g of bis(chloromethylsilyl)ethane (compound 1) was then added dropwise over 2 hours using a dropping funnel, with the flask being kept in a water bath at 25° C. After the addition, the mixture was stirred for 2 hours.

The sodium salt produced as a by-product was filtered using a glass filter covered with celite, and the salt was washed with 200 ml of hexane. The filtrate was concentrated using an evaporator under reduced pressure to obtain 95 g (yield: 80%) of bis(dimethoxymethylsilyl)ethane (compound 3).

The residual water content of the end product was 100 ppm. The content (metal impurity content) of elements other than silicon, carbon, oxygen, and hydrogen was as follows. Specifically, the Na content was 4 ppb, the K content was 3 ppb, the Fe content was 3 ppb, and the Ni content was 2 ppb. The content of each of Li, Fe, Cr, Ag, Cu, Zn, Mn, Co, Ti, Zr, Al, Pb, Sn, and W was equal to or less than the detection limit (0.2 ppb).

2.2.5. Synthesis Example 5

A three-necked flask equipped with a cooling condenser and a dropping funnel was dried at 60° C. under reduced pressure, and filled with nitrogen.

The flask was charged with 59 g of sodium methoxide (compound 2) and 153 g of methanol, and the mixture was stirred for 15 minutes at 300 rpm using a 3:1 motor. A solution of 88 g of p-(dichlorosilyl)benzene (compound 1) dissolved in 100 g of tetrahydrofuran was added dropwise over 2 hours using a dropping funnel, with the flask being kept in a water bath at 25° C. After the addition, the mixture was stirred for 2 hours.

The sodium salt produced as a by-product was filtered using a glass filter covered with celite, and the salt was washed with 200 ml of hexane. The filtrate was concentrated using an evaporator under reduced pressure to obtain 121 g (yield: 75%) of bis(trimethoxysilyl)benzene (compound 3).

The residual water content of the end product was 89 ppm. The content (metal impurity content) of elements other than silicon, carbon, oxygen, and hydrogen was as follows. Specifically, the Na content was 6 ppb, the K content was 7 ppb, the Fe content was 6 ppb, and the Ni content was 4 ppb. The content of each of Li, Fe, Cr, Ag, Cu, Zn, Mn, Co, Ti, Zr, Al, Pb, Sn, and W was equal to or less than the detection limit (0.2 ppb).

2.2.6. Comparative Synthesis Example 1

A three-necked flask equipped with a cooling condenser and a dropping funnel was dried at 60° C. under reduced pressure, and filled with nitrogen.

The flask was charged with 153 g of methanol and stirred for 15 minutes at 300 rpm using a 3:1 motor. 86 g of bis(methylchlorosilyl)methane (compound 1) was then added dropwise over 2 hours using a dropping funnel, with the flask being kept in a water bath at 25° C. After the addition, the mixture was stirred for 2 hours.

The filtrate was concentrated using an evaporator under reduced pressure to obtain 14 g (yield: 6%) of bis(dimethoxymethylsilyl)methane (compound 3).

2.2.7. Comparative Synthesis Example 2

A three-necked flask equipped with a cooling condenser and a dropping funnel was dried at 50° C. under reduced pressure, and was charged with nitrogen.

The flask was charged with 29.04 g of magnesium. After the addition of 96 g of tetrahydrofuran, 4.0 g of chloromethylmethyldimethoxysilane (raw material for the compound 6) was added to the mixture at room temperature with stirring. A reaction started after 10 minutes, and the temperature of the reaction solution increased to 50° C. After the addition of 150 g of tetrahydrofuran to the reaction solution, the flask was immersed in a bath kept at 25° C., and the content was stirred for five minutes.

A solution prepared by dissolving 176 g of chloromethylmethyldimethoxysilane (raw material for compound 6) and 250 g of methyltrimethoxysilane (compound 7) in 200 g of tetrahydrofuran was then added dropwise to the reaction solution in the flask over 120 minutes. A white precipitate was observed when 20 minutes had elapsed after the start of addition. After the addition, the temperature of the bath was increased to 70° C., and the mixture was allowed to react for three hours.

After the reaction, a magnesium salt obtained as a by-product was filtered using a Kiriyama funnel, and washed with 200 ml of hexane. The filtrate was concentrated under reduced pressure using an evaporator, and then distilled to obtain 10 g (yield: 3.8%) of bis(dimethoxymethylsilyl)methane (compound 3) as the end product.

Synthesis Examples 2 to 5 show that the compound 3 can be obtained in high yield by the reaction of the compound 1 and the compound 2.

On the other hand, it can be seen that when the compound 3 is produced by the reaction of the compound 1 and an alcohol instead of the compound 2 as in the Comparative Synthesis Example 1 or by a Grignard reaction as in the Comparative Synthesis Example 2, the yield of the compound 3 is unduly low.

According to the method of producing the organosilicon compound of the invention, the compound 3 can be produced by a simple manner in high yield by the reaction of the compound 1 and compound 2.

The embodiments according to the invention have been described above. The invention includes various other configurations substantially the same as the configurations described in connection with the embodiments (such as a configuration having the same function, method, and results, or a configuration having the same objective and results). The invention also includes a configuration in which an unsubstantial section (part) described in connection with the embodiments is replaced by another section (part). The invention also includes a configuration having the same effects as those of the configurations described in connection with the embodiments, or a configuration capable of achieving the same objective as that of the configurations described in connection with the embodiments. Further, the invention includes a configuration in which a known technique is added to the configurations described in connection with the embodiments.

Although only some embodiments of the invention have been described in detail above, those skilled in the art would readily appreciate that many modifications are possible in the embodiments without materially departing from the novel teachings and advantages of the invention. Accordingly, such modifications are intended to be included within the scope of the invention.

What is claimed is:

1. A method of producing an organosilicon compound comprising: reacting a compound shown by the following formula (4) and a compound shown by the following formula (5) to produce a compound shown by the following formula (1); and reacting the compound shown by the following formula (1) and a metal compound shown by the following formula (2) to produce an organosilicon compound shown by the following formula (3),

$$R^2{}_n X_m Si-R^1-SiX_m R^2{}_n \qquad (1)$$

wherein $R^1$ represents a methylene group, an alkylene group having 2 to 10 carbon atoms, or an arylene group having 6 to 12 carbon atoms, $R^2$ individually represents an alkyl group having 1 to 10 carbon atoms, an alkenyl group having 2 to 10 carbon atoms, an alkynyl group having 2 to 10 carbon atoms, or an aryl group having 6 to 12 carbon atoms, X individually represents a hydrogen atom or a halogen atom, and m and n individually represent an integer from 0 to 3, provided that m+n=3, at least one m being 1 or more,

$$M(OR^4)_r \qquad (2)$$

wherein M represents a metal element, r represents the valence of the metal element, and $R^4$ individually represents an alkyl group having 1 to 10 carbon atoms, an alkenyl group having 2 to 10 carbon atoms, an alkynyl group having 2 to 10 carbon atoms, or an aryl group having 6 to 12 carbon atoms,

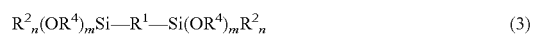

$$R^2{}_n(OR^4)_m Si-R^1-Si(OR^4)_m R^2{}_n \qquad (3)$$

wherein $R^1$, $R^2$, m, and n are the same as defined for the formula (1), and $R^4$ is the same as defined for the formula (2),

 (4)

wherein Y represents a halogen atom, and $R^1$ is the same as defined for the formula (1),

 (5)

wherein X, $R^2$, m, and n are the same as defined for the formula (1).

2. The method of producing an organosilicon compound according to claim 1, wherein $R^1$ in the formula (1) and the formula (3) is a methylene group.

3. The method of producing an organosilicon compound according to claim 1, wherein M in the formula (2) is at least one metal element selected from an alkali metal element and an alkaline earth metal element.

4. The method of producing an organosilicon compound according to claim 3, wherein M in the formula (2) is sodium.

5. The method of producing an organosilicon compound according to claim 1, wherein $R^2$ in the formula (1) individually represents an alkyl group having 1 to 10 carbon atoms, an alkenyl group having 2 to 10 carbon atoms, or an aryl group having 6 to 12 carbon atoms.

6. The method of producing an organosilicon compound according to claim 5, wherein $R^2$ in the formula (1) individually represents an alkyl group having 1 to 10 carbon atoms or an alkenyl group having 2 to 10 carbon atoms.

7. The method of producing an organosilicon compound according to claim 6, wherein $R^2$ in the formula (1) individually represents an alkyl group having 1 to 10 carbon atoms.

* * * * *